US00PP11771P2

(12) United States Plant Patent
van Rijn

(10) Patent No.: US PP11,771 P2
(45) Date of Patent: Feb. 6, 2001

(54) ANTHURIUM PLANT NAMED 'FANTASY LOVE'

(75) Inventor: Leonardus van Rijn, Schipluiden (NL)

(73) Assignee: Rijnplant, Schipluiden (NL)

( * ) Notice: Under 35 U.S.C. 154(b), the term of this patent shall be extended for 0 days.

(21) Appl. No.: 09/291,110

(22) Filed: Apr. 14, 1999

(51) Int. Cl.[7] ..... A01H 5/00
(52) U.S. Cl. ..... Plt./367
(58) Field of Search ..... Plt./367, 365, 368

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Anthurium plant named 'Fantasy Love', characterized by its upright and outwardly spreading plant habit; freely clumping growth habit, dense and bushy plants; durable dark green leaves that are ovate in shape; numerous inflorescences that are positioned upright and beyond the foliage on strong and erect scapes; durable pink red spathes that become green with development; year-round continuous flowering; good flower development under low light conditions; and good post-production longevity.

1 Drawing Sheet

BACKGROUND OF THE INVENTION

The present invention relates to a new and distinct cultivar of Anthurium plant, botanically known as *Anthurium andreanum*, and hereinafter referred to by the cultivar named Fantasy Love.

The new Anthurium is a product of a planned breeding program conducted by the Inventor in Schipluiden, The Netherlands. The objective of the program is to create and develop new Anthurium cultivars that have a freely clumping growth habit, strong and vigorous plant growth, attractive spathe color, numerous inflorescences and leaves, and good post-production longevity.

The new Anthurium originated from a cross by the Inventor on Mar. 2, 1995 ,in a laboratory in Belgium, of the Inventor's proprietary *Anthurium andreanum* selection code number 94-20 as the female, or seed, parent with the Inventor's proprietary *Anthurium andreanum* selection code number 92-26 as the male, or pollen, parent. The cultivar Fantasy Love was discovered and selected by the Inventor as a plant within the progeny of the stated cross in a controlled environment in Schipluiden, The Netherlands in May, 1997.

Asexual propagation of the new cultivar by tissue culture has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar Fantasy Love. These characteristics in combination distinguish 'Fantasy Love' as a new and distinct cultivar:

1. Upright and outwardly spreading plant habit.
2. Freely clumping growth habit, dense and bushy plants.
3. Durable dark green leaves that are ovate in shape.

4. Numerous inflorescences that are positioned upright and beyond the foliage on strong and erect scapes.
5. Durable pink red spathes that become green with development.
6. Year-round continuous flowering.
7. Good flowering under low light conditions.
8. Good post-production longevity.

The new Anthurium can be compared to the female parent, the Inventor's proprietary selection code number 94-20. In side-by-side comparisons conducted by the Inventor in Schipluiden, The Netherlands, plants of the new Anthurium differ from plants of selection code number 94-20 in the following characteristics:

1. Plants of the new Anthurium are more compact than plants of the selection code number 94-20.
2. Plants of the new Anthurium have larger and darker green leaves than plants of the selection code number 94-20.
3. Plants of the new Anthurium are more floriferous than plants of the selection code number 94-20.

The new Anthurium can be compared to the male parent, the Inventor's proprietary selection code number 92-26. In side-by-side comparisons conducted by the Inventor in Schipluiden, The Netherlands, plants of the new Anthurium differ from plants of selection code number 92-26 in the following characteristics:

1. Plants of the new Anthurium are not as freely clumping as plants of the selection code number 92-26.
2. Plants of the new Anthurium have smaller spathes than plants of the selection code number 92-26.

The new Anthurium can be compared to the Anthurium cultivar Champion, disclosed in U.S. Plant Pat. No. 9,088. In side-by-side comparisons conducted by the Inventor in Schipluiden, The Netherlands, plants of the new Anthurium differ from plants of the cultivar Champion in the following characteristics:

1. Plants of the new Anthurium grow faster than plants of the cultivar Champion.
2. Plants of the new Anthurium are more freely clumping than plants of the cultivar Champion.

3. Plants of the new Anthurium have rougher leaves than plants of the cultivar Champion.

4. Plants of the new Anthurium and of the cultivar Champion differ in spathe shape and color.

BRIEF DESCRIPTION OF THE PHOTOGRAPH

The accompanying colored photograph illustrates the overall appearance of the new Anthurium, showing the colors as true as it is reasonably possible to obtain in colored reproductions of this type. The photograph comprises a side perspective view of a typical potted plant of the cultivar Fantasy Love. Leaf, spathe and spadix colors in the photograph may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe three-year old plants grown in 30-cm conatiners in Schipluiden, The Netherlands, in a glass greenhouse with an average day temperature of 25° C. and an average night temperature of 19° C.

Botanical classification: *Anthurium andreanum* cultivar Fantasy Love.

Parentage:

*Female parent.*—Inventor's proprietary *Anthurium andreanum* selection code number 94-20.

*Male parent.*—Inventor's proprietary *Anthurium andreanum* selection code number 92-26.

Propagation:

*Method.*—By tissue culture.

*Time to initiate roots.*—About 70 or 84 days at 24° C. or 21° C., respectively, from a tissue cultured plantlet in a laboratory in Belgium.

*Root description.*—Numerous and very strong fleshy roots.

Plant description:

*Plant shape.*—Upright and outwardly spreading, inverted triangle, symmetrical.

*Growth habit.*—Freely clumping, bushy and dense plants. Appropriate for 12 to 20-cm containers.

*Plant height.*—About 60 to 80 cm from soil level to apex of spathes.

*Plant width.*—About 60 cm.

*Plant vigor.*—High.

*Growth rate.*—Rapid.

*Crop time.*—About 6 and 12 months are usually required from planting of young plants to finished plants in 12 and 20-cm containers, respectively.

*Foliage description.*—Quantity: Usually about four leaves per shoot. Length: About 17 to 20 cm. Width: About 11 to 13 cm. Shape: Ovate. Apex: Apiculate to cuspidate. Base: Auriculate; lobes not overlapping. Margin: Entire; undulating. Texture: Smooth, glabrous, leathery. Color: Young leaves, upper surface: Darker than 147A; glossy. Young leaves, lower surface: 137C with some gray. Mature leaves, upper surface: Darker than 147A; dull. Mature leaves, lower surface: 146D. Petiole: Length: About 32 to 40 cm. Color: Close to 146B with slight reddish brown anthocyanin coloring. Geniculum length: About 2 to 3 cm. Geniculum diameter: About 3 to 5 mm. Geniculum color: 144D; older leaves with dark reddish brown anthocyanin coloring.

Inflorescence description:

*Inflorescence arrangement.*—Spathes with spadices held beyond the foliage. Flowering structures arise from leaf axils. Freely flowering; continuous flowering year-round; numerous spathes/spadices per plant.

*Inflorescence longevity.*—Spathes/spadices last about six weeks under winter conditions and about three months under summer conditions; persistent.

*Flowers.*—Quantity per spadix: Numerous, about 200. Shape: Rounded. Diameter: About 1 mm, maximum.

*Spathe.*—Length: About 8 to 10 cm. Width: About 10 to 12 cm. Shape: Broadly cordate. Apex: Apiculate. Base: Straight. Margin: Entire. Texture: Leathery, glabrous, slight blistering, glossy when young becoming duller with development. Color: When opening: White, 155C, with pinkish flush, 49C. Front surface: Center, 48B to 50B; pink red becoming green, 144C, with development; with subesequent development, green areas become darker, 144A to 144B and larger; veins maintain reddish coloration. Back surface: Center, 49C to 49D; pink becoming green, 144C, with development; with subsequent development green becoming darker, 144A to 144B; veins maintain reddish coloration. After senescence: 144A; veins, close to 51B.

*Spadix.*—Length: About 7 to 8 cm. Diameter: Midsection, about 8 cm; apex, about 5 mm. Shape: Columnar. Cross section: Rounded. Longitudinal axis: Very weakly recurved. Color: Base: 28B to 28C. Mid-section: 47C. Apex: 47B. After senescence: 144A.

*Scape.*—Length: About 50 to 60 cm. Aspect: Strong and erect. Color: Base, green, 144A; apex, becoming purplish with anthocyanin coloring.

*Reproductive organs.*—Androecium: Pollen color: Creamy white, 158D. Gynoecium: Stigma shape: Ovoid. Ovary: Protogynous.

Disease resistance: Plants of the new Anthurium have exhibited good resistance to root diseases common to Anthurium.

Seed development: Seed development on plants of the new Anthurium has not been observed.

It is claimed:

1. A new and distinct cultivar of Anthurium plant named 'Fantasy Love', as illustrated and described.

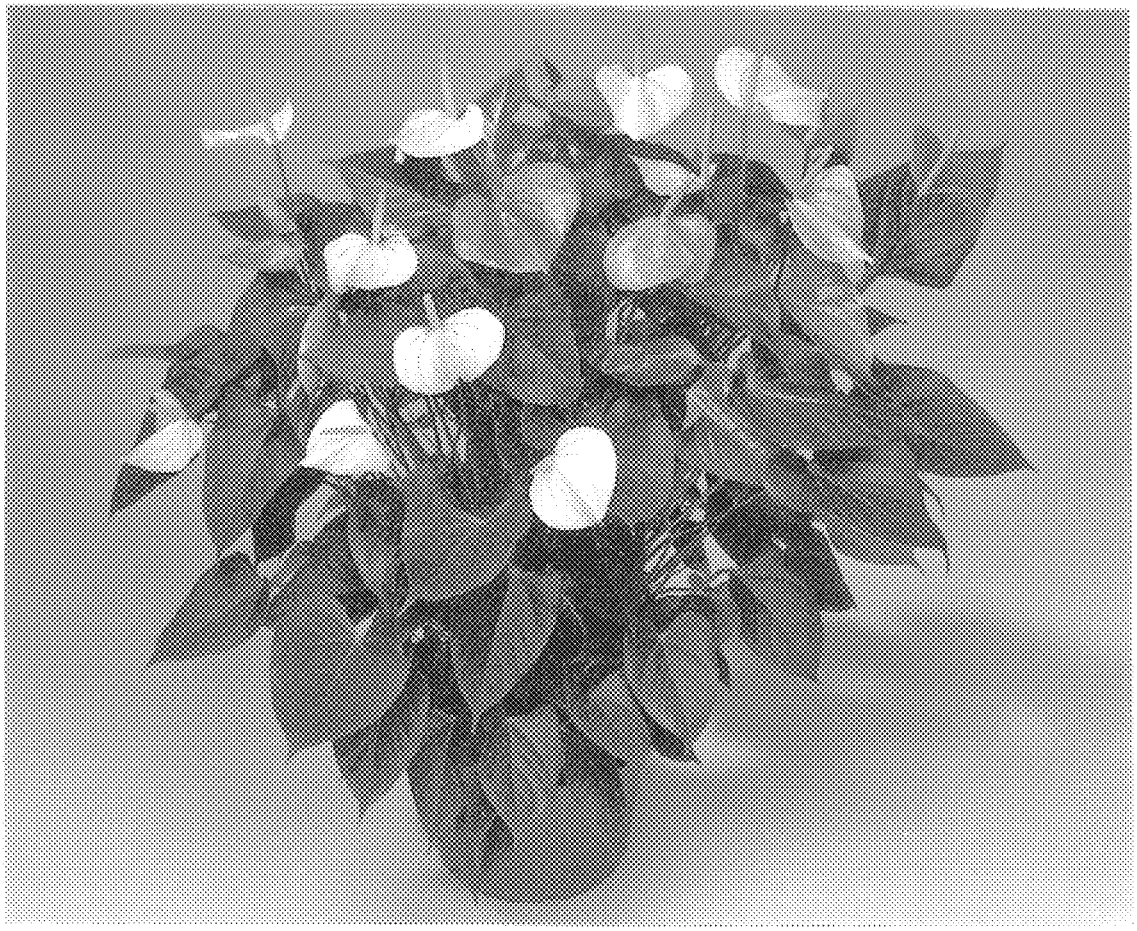

* * * * *